United States Patent [19]
Brandt et al.

[11] Patent Number: 5,420,047
[45] Date of Patent: May 30, 1995

[54] METHOD FOR CARRYING OUT IMMUNODIAGNOSTIC TESTS

[75] Inventors: Heinz-Dieter Brandt; Rolf Dhein; Karlheinz Hildenbrand, all of Krefeld; Ronald Stöcker, Hilden, all of Germany

[73] Assignee: Bayer Aktiengesellschaft, Leverkusen, Germany

[21] Appl. No.: 149,247

[22] Filed: Nov. 12, 1993

[30] Foreign Application Priority Data

Nov. 13, 1992 [DE] Germany ............ 42 38 389.7

[51] Int. Cl.⁶ ............ G01N 33/53; G01N 33/545
[52] U.S. Cl. ............ 435/7.9; 436/518; 436/531; 436/810; 435/4; 435/7.92; 435/28; 435/970; 435/805; 422/56
[58] Field of Search ............ 435/7.9, 7.92, 7.94, 435/970, 805, 25, 28, 4; 436/518, 528, 531, 810, 532; 422/56, 57, 60.1, 69

[56] References Cited

U.S. PATENT DOCUMENTS

| | | | |
|---|---|---|---|
| 4,772,635 | 9/1988 | Mitschker et al. | 521/34 |
| 4,968,430 | 11/1990 | Hildenbrand et al. | 210/640 |
| 5,122,452 | 1/1992 | Yamazaki et al. | 435/7.93 |
| 5,124,128 | 6/1992 | Hildenbrand et al. | 422/56 |
| 5,160,436 | 11/1992 | Hildenbrand et al. | 422/56 |

FOREIGN PATENT DOCUMENTS

| | | |
|---|---|---|
| 0186347 | 7/1986 | European Pat. Off. |
| 0225535 | 6/1987 | European Pat. Off. |
| 243876 | 11/1987 | European Pat. Off. |
| 3809523 | 10/1988 | Germany |
| 8607345 | 12/1986 | WIPO |

OTHER PUBLICATIONS

H. V. Bergmeyer, Methods of Enzymatic Analysis, vol. I, 3rd, ed., Verlag Chemie, pp. 197–232.
Chemical Abstracts, vol. 107, No. 21, 23. Nov. 1987, Columbus, Ohio, USA P. Hermann et al. "Immobilization of Proteins on Macro Porous Polymeric Carriers: use of salts to increase covalent coupling".

*Primary Examiner*—Carol E. Bidwell
*Attorney, Agent, or Firm*—Sprung Horn Kramer & Woods

[57] ABSTRACT

Immunodiagnostic tests in which enzymes or antibodies are bound to porous carrier materials can be carried out by employing as porous carrier materials macroporous polymer membranes which are prepared by (a) dispersing an insoluble filler in a solution which contains at least two incompatible polymers in amounts which lead to phase separation in the solution, resulting in a homogeneous casting solution, and (b) applying this solution to a support and carrying out a precipitation coagulation.

13 Claims, 3 Drawing Sheets

METHOD FOR CARRYING OUT IMMUNODIAGNOSTIC TESTS

BACKGROUND OF THE INVENTION

1. Field of the Invention

The present invention relates to a method for carrying out immunodiagnostic tests in which enzymes or antibodies are bound to porous carrier materials. The method according to the invention is characterized by the use of macroporous polymer membranes as such porous carrier materials. The macroporous polymer membranes are prepared by preparing a homogeneous casting solution by dispersing an insoluble filler in a solution which contains at least two incompatible polymers in amounts which lead to phase separation in the solution, applying this solution to a support, and then carrying out a precipitation coagulation.

Porous carrier materials which bind biologically active proteins such as enzymes or antibodies play an important part in various technical sectors and in clinical diagnosis. In this context the immunoassay methods are particularly important. The most widely used are competitive binding assays (RIA, EIA) and sandwich assays (IRMA, ELISA), with the ELISAs becoming increasingly important. In the ELISA (Enzyme Linked Immunosorbent Assay), the antigen to be determined is bound by a carrier-bound antibody (primary antibody) and quantitatively determined by an enzymatic second antibody (secondary antibody).

2. Description of the Related Art

The basic principle of these detection methods is described in numerous publications (Angew. Chemie 97 (1985), 141–163; Chimia 29 (3) (1975), 109). The iramobilization (binding) of the primary antibody to the porous matrix surface can in principle take place in two different ways, namely by adsorption or covalent bonding, and both methods have advantages and disadvantages. Whereas the risk of denaturation of the biochemical agents is small in the case of adsorption, there is a risk of washing out or leaching out when the assay is carried out; precisely the converse applies to the covalent method. This is why the aim is to be able to use alternative methods (both adsorptive and covalent) depending on the example of use and assay method.

Detection of the immunochemical assay reaction in the case of the ELISA method frequently takes place by a chromogenic reaction which is catalyzed by an enzyme which is located on the secondary antibody. Thus, for example, secondary antibodies labelled with peroxidase (POD) are frequently employed and, in the presence of $H_2O_2$, induce an oxidation reaction, whereupon a colour change takes place. The chromogen is impregnated into the matrix during the course of the assay procedure, and in the case of POD-catalyzed reactions the well-known water-soluble trinder system 4-aminoantipyrine/2-hydroxy-3,5-dichlorobenzenesulphonate (H.V. Bergmeyer, Methods of Enzymatic Analysis, Vol. I, 3rd. ed., Verlag Chemie) is frequently used.

Other enzyme/chromogen systems are: alkaline phosphatase/p-nitrophenyl phosphate or β-galactosidase/o-nitrophenyl galactoside. Companies marketing membrane systems for immunodiagnosis are, for example, Millipore (product: IMMUBILON®) or PALL (product: IMMUNUDYNE®) in combination with brochures which describe the assay procedure. The complete assay consists of a plurality of incubation and washing steps, with the iramobilization of the primary antibody as a rule taking place by covalent bonding. Microtiter plates or dot-blot apparatuses are available for carrying out the assays, for example from Bio Rad. Critical problems in carrying out the assays are washing out and leaching out, it being possible for the substances and agents which have previously been introduced to be washed out again during a plurality of impregnation and washing steps. This is particularly critical with the chromogens employed to date which, as a rule, cannot be covalently bonded and undergo considerable extraction, because their solubility in water is often good, in the subsequent washing procedures.

This frequently leads to falsification of the results of measurement and reduction in the sensitivity.

It was therefore desirable to have available membrane matrices for immunochemical detection reactions which are particularly suitable for the ELISA method and which display the following features:
a) possibility of both adsorptive and covalent immobilization,
b) possibility of covalent iramobilization in a simple and non-damaging way and
c) improved immobilization of the chromogen for substantial prevention of leaching out of the reaction colours.

It has now been found, surprisingly, that macroporous membranes composed of polymer blends described in German Offenlegungsschrift 38 09 523 are outstandingly suitable for immunodiagnostic test methods.

SUMMARY OF THE INVENTION

A method for carrying out immunodiagnostic tests in which enzymes or antibodies are bound to porous carrier materials has been found and is characterized in that the porous carrier materials employed are macroporous polymer membranes which are prepared by
a) dispersing insoluble fillers in a solution which contains at least two incompatible polymers in amounts which lead to phase separation in the solution, resulting in a homogeneous casting solution, and
b) applying this solution to a support and carrying out a precipitation coagulation.

BRIEF DESCRIPTION OF THE DRAWINGS

The accompanying

DETAILED DESCRIPTION OF THE INVENTION

Figure 1:
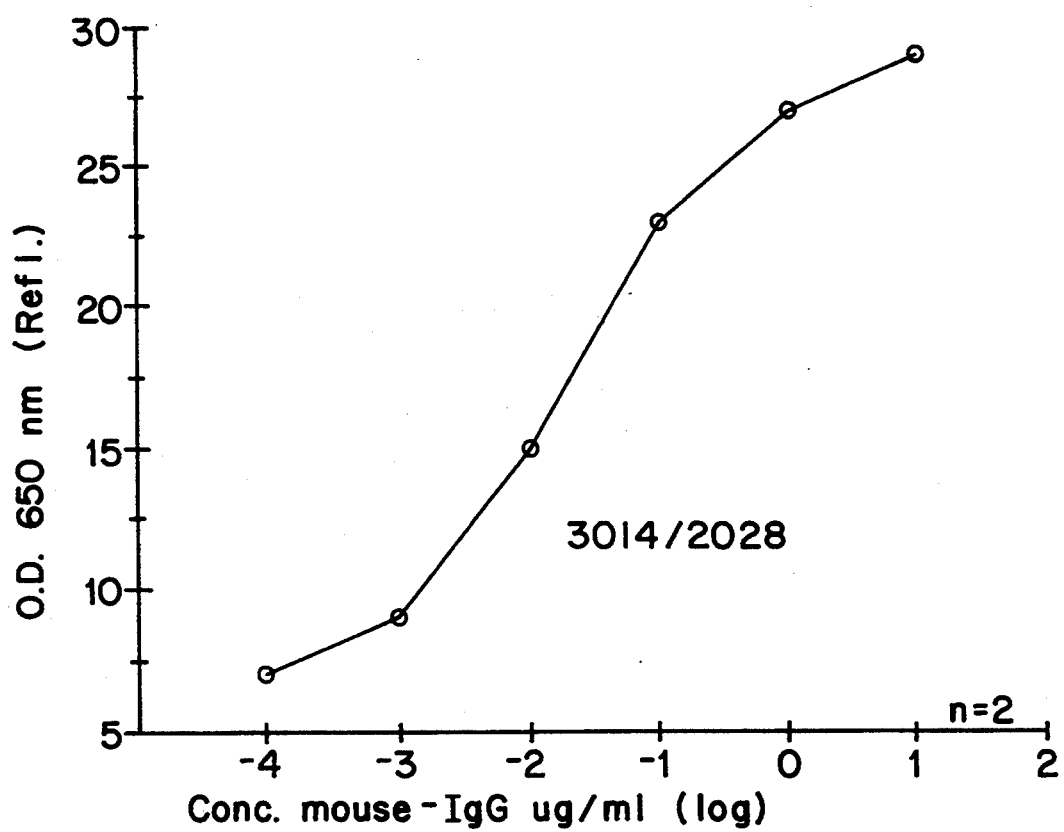
FIGS. 1–3 present the results of the binding experiments forth in Example 2.

If, for example, a 20% by weight solution of polyurethane in dimethylformamide (PU/DMF solution) and a 20% by weight solution of polyacrylonitrile in dimethylformamide (PAN/DMF solution) are mixed with stirring, phase separation takes place after brief standing. Mixtures of this type are unstable and are unsuitable as casting solutions for preparing the membranes.

By contrast, if the same polymer/DMF solutions are combined with fillers, for example talc, being dispersed simultaneously or subsequently, stable homogeneous casting solutions which are suitable for membrane preparation by the precipitation coagulation method are obtained. By comparison with known membranes, those prepared from casting solutions of this type surprisingly show distinctly larger pores on the surface, a very much higher overall porosity and a distinctly increased absorptive capacity which is comparable with that of chromatography papers.

Electron micrographs of the cross-section of these polymer membranes show that they are structures with a felt-like texture, while the asymmetric structure texture with the dense polymer skin on the membrane surface is almost completely suppressed. In the case of a membrane with the described texture, pore diameters of up to 30 μm are evident on the membrane surface.

The polymer casting solutions required for preparing macroporous membrane matrices of this type must fulfil the following conditions:

the solutions of the individual polymer components must not be mutually miscible. In the case of mutually miscible systems, in analogy to casting solutions hitherto disclosed, microporous membrane structures with a pronounced asymmetric structure are obtained;

the solvents for the individual polymer components must be mutually miscible;

in order to convert the immiscible polymer components into homogeneous casting solutions it is necessary for suitable insoluble fillers for example, inorganic fillers to be dispersed in.

Examples of suitable fillers are: talc, titanium dioxide, barium sulphate, silicon dioxide, microcrystalline cellulose, zeolites, bentonites, calcium carbonate, magnesium carbonate, zinc oxide, iron oxides, preferably talc, titanium dioxide, bariran sulphate, highly disperse silica (for example Aerosils from Degussa), quartz, microcrystalline cellulose, zeolites and bentonites. Inorganic and organic fillers of these types are commercially available. Not all the said fillers are equally suitable for all polymer combinations. Thus, for example, casting solutions composed of polyurethane/polyacrylonitrile mixtures are less stable with titanium dioxide or barium sulphate and show a detectable inhomogeneity, whereas solutions of the same polymer combination with talc result in good homogeneity and dispersion stability. It is also p9ssible to employ mixtures of a plurality of the said fillers. The surface of the fillers which are employed can be organically modified where appropriate. For example, hydrophobic highly disperse silicas (AEROSIL R 972 ® from Degussa) or amine-modified types are commercially available.

The amount of the fillers which are employed depends on their specific surface areas but is generally in the range from 5 to 500% by weight based on the total weight of the organic substance in the membrane. In the case of highly disperse fillers, for example AEROSIL 200 ® (200 m²/g), amounts in the range from 5 to 50% by weight based on the weight of the organic substance in the membrane are sufficient. In the case of fillers with lower specific surface areas in the region of a few m²/g it is possible for the amount of the fillers which is employed to be in the range from 35% to 500% based on the weight of the organic substance in the membrane. The preferred range for highly disperse fillers is 10 to 25% by weight, and that for fillers with lower specific surface areas is 50 to 200% by weight.

Examples of suitable polymer combinations are the following:
- cellulose esters/polyvinyl esters
- polyurethane/polyacrylic derivatives or acrylic copolymers
- polycarbonate copolymers/polyurethane
- polyvinyl derivatives/polysulphones
- polyamides or polyimides/polystyrene or styrene copolymers
- poly-para-dimethylphenylene oxide/polyvinylidene fluoride
- poly sul phone/poly acrylonitrile
- poly(ethersulphone)/anionically modified polyacrylonitrile.

Other combinations of the said polymer systems are also possible and may, furthermore, be extended to ternary polymer mixtures.

Specific examples of such polymer combinations are: cellulose acetate/polyvinyl acetate (for example MOWILITH®), polyurethane (DESMODERM KBH®)/polyacrylonitrile (DRALON T®), DESMODERM KBH®/aminemodified dralon (DRALON A®), DESMODERM KBH®/anionically modified dralon (DRALON U®), polysulphone (UDEL P 1700®)/polyvinylidene fluoride, polyether carbonate/DESMODERM KBH®, DRALON U®/MOWILITH®, cellulose acetate/DRALON U®, cellulose acetate/DRALON U®/polystyrene, MOWILITH®/DESMODERM KBH®/polyvinyl chloride and poly(ethersulphone) (ULTRASON E®)-/polyacrylonitrile (DRALON X®).

The ratio of the amounts of the copolymers in the particular combinations which is necessary for phase separation without the filler dispersed in can be found by simple preliminary tests.

Another very important ternary polymer system is DESMODERM KBH®/MOWILITH®/DRALON T®, it also being possible to replace DRALON T® by DRALON A® or DRALON U®. The chemical structures of the polymers which are preferably employed are described in the appendix to the exemplary embodiments.

Suitable for the preparation of the polymer casting solutions are, for example, dimethylformamide (DMF), N-methylpyrrolidone (NMP), dimethyl sulphoxide (DMSO), dimethylacetamide, dioxolane, dioxane, acetone, methyl ethyl ketone, CELLOSOLVE® or mixtures of these solvents.

The overall process for preparing the membranes can be represented by the following example: the DMF polymer solutions composed of DESMODERM KBH®, MOWILITH® and DRALON®, which are in each case about 20% by weight, are mixed while dispersing in talc with the aid of a high-speed stirrer (dissolver) to give a homogeneous polymer casting solution. After degassing in vacuo, the casting solution is applied with the aid of a knife in a layer thickness of, for example, 150 μm to a support substrate and immersed in the coagulation bath, preferably pure water. After a residence time of about 2 minutes, the polymer membrane which is produced thereby is removed from the coagulation bath and dried with hot air.

Other components for the preparation of the macroporous membranes can be surfactants, for example dioctyl sodium sulphosuccinate or dodecylbenzenesulphonates which are used in the casting solution. It is likewise possible for water-soluble polymers such as cellulose ethers, polyethylene glycols, polyvinyl alcohol or polyvinylpyrrolidone to be components of the polymer casting solution. Suitable additives furthermore are socalled coagulation aids such as, for example, cationic polyurethane dispersions.

The casting solution is applied to ,a support in order to be able to carry out the precipitation coagulation and to be able to manipulate the casting solution and the macroporous polymer. Such supports can be, for example, glass or siliconized carrier materials of a wide variety of origins. Other carrier materials are liquidpermeable polymer woven or polymer nonwoven fabrics on which the macroporous polymer membrane shows good adhesion.

Macroporous polymer membranes which are employed according to the invention have average pore diameters of 10 to 50 μm, preferably 10 to 30 μm. Membranes which are particularly advantageous for carrying out immunodiagnostic tests are those into which the chromogen has already been integrated during the membrane preparation. An important example thereof is the chromogert 3,3',5,5'-tetramethylbenzidine (TMB) which is a known oxidation indicator. Compared with known conventional system, two important advantages emerge:

1. The overall test procedure is reduced by the step of indicator impregnation and thus simplified. This aspect is important inasmuch as organic solvents are employed as solvents for many indicators, including TMB for example, and may damage either the polymer membrane or the biochemical reagent system.

2. An even more important advantage of the indicator integrated into the membrane is that the leaching out of the indicator colour produced in the reaction is virtually completely suppressed, in contrast to conventional systems.

The method according to the invention using the macroporous polymer membranes described surprisingly results in possibilities for improved adsorptive and covalent binding of biochemical agents (enzymes, antibodies):

a) Adsorptive immobilization

It surprisingly emerges that the adsorptive binding property of the macroporous polymer membranes described can be considerably increased by a modification of the membrane surface with free amino groups. The amine-modified membranes can be prepared either by subsequent treatment of the finished membrane or, preferably, by additives in the polymer casting solution employed to prepare the membrane by the method of precipitation coagulation in water. Additives which have proved to be suitable are polymers with free amino groups such as, for example, polyethyleneimine. Examples of other suitable additives are polyamide-amines or other watersoluble amine-containing polymers as employed, for example, also as retention agents in paper manufacture (Das Papier 33, No. 10A). Such retention agents are commercially available, for example, under the name RETAMINOL ® (Bayer AG) or PRAESTOL ® (Stockhausen).

Although such additives are water-soluble compounds, they are surprisingly not extracted during the course of membrane preparation by coagulation in water. This fact can be demonstrated by the ninhydrin reaction.

It has furthermore been found that amino-modified membranes can also be prepared in a straightforward manner by adding amine-modified fillers to the polymer casting solution. Suitable examples thereof are: silicate fillers whose surface is treated with aminosilane. Products of this type are marketed, for example, as Silbond 600 AST (from Quartz-Werke). It has emerged in this connection that particularly good results in respect of adsorptive iramobilization are achieved by a combination of the additives polyethyleneimine and silicates treated with aminosilanes.

b) Covalent immobilization

It has furthermore been found that the described amine-modified macroporous polymer membranes are also outstandingly suitable for covalent iramobilization of the biochemical reagents. In this connection. it has been found, surprisingly, that, besides the known coupling reagents such as glutaraldehyde, carbodiimides or bishydroxysuccinimides, very particulafiy suitable as covalent anchor groups are water-soluble bisulphite adducts of polyfunctional isocyanates. Bisulphite adducts of this type and their preparation are known (Houben-Weyl, Methoden der organischen Chemie (Methods of organic chemistry), Vol. 14/2, pages 63–64). They can be obtained by reacting isocyanates with sodium bisulphite. Suitable isocyanates are preferably polyfunctional and can be aliphatic, cycloaliphatic or aromatic. Examples of suitable polyisocyanates are: hexamethylene diisocyanate, 1,4-diisocyanatocyclohexane, 2,4- and 2,6-toluylene diiso cyanate and their mixtures, 1-isocyanatomethyl-5-isocyanato-1,3,3-trimethylcyclohexane, 2,2,4- and 2,4,4-trimethylhexamethylene 1,6-diisocyanate, 1,5-diisocyanatonaphthalene, 1,3-cyclopentylene diisocyanate, m- and p-phenylene diisocyanate, 2,4,6-triisocyanatotoluene, tris(4-isocyanatophenyl)methane, 1,3- and 1,4-xylylene diisocyanate, 3,3'-dimethyl-4,4'-diphenylene diisocyanate, diisocyanatodurene, 1-phenoxy-2,4'-phenylene diisocyanate, 1-tert.-butyl-2,4-phenylenediisocyanate, methylenebis 4,4'-cyclohexyl diisocyanate, 1-chloro-2,4-phenylene diisocyanate and bis(4-isocyanatophenyl) ether; other polyisocyanates which are not mentioned here are known in principle to the person skilled in the art.

It is furthermore possible to employ higher molecular weight and, where appropriate, also more highly functional polyisocyanates which are prepared from lower molecular weight basic components by polymerization reaction to give uretdiones or isocyanurate derivatives. Examples which may be mentioned are the uretdione from 2 mol of 2,4-toluylene diisocyanate and polymerization products which contain diisocyanurate rings and are derived from 2,4- and 2,6-toluylene diisocyanate or hexamethylene diisocyanate, a system which contains an average of two isocyanurate rings in the molecule and is formed from 5 mol of toluylene diisocyanate, or a corresponding derivative composed of an average of 2 mol of toluylene diisocyanate and 3 mol of hexamethylene diisocyanate. It is possible according to another method of construction to prepare from di- or polyisocyanates, by partial hydrolysis via the stage of the carbamic acid and of the amine, higher biuret-linked systems, for example a biuret-linked compound which is formally derived from 3 mol of hexamethylene diisocyanate with the addition of 1 mol of water and elimination of 1 mol of carbon dioxide. Polyisocyanates which are likewise suitable are obtained on reaction of di- and polyols with di- or polyfunctional isocyanates when the molar ratio of hydroxy compounds to the isocyanate is selected so that free NCO functionalities always remain present in the randomly formed reaction products, and a molecular weight of 2000 to 3000 is not exceeded. Similar suitable polyisocyanates are obtained from polyesters which contain hydroxyl groups by reaction with excess di- or polyfunctional isocyanates. All the di- and polyisocyanates described above can be reacted in this way with di- and polyols such as mono- and polyethylene glycol, propanediols, butanediols, neopentyl glycol and other pentanediols, adipol, hexanediols, cyclohexanediols, 1,4-dihydroxynaethylcyclohexane, perhydrobisphenol A, glycerol, trimethylolLeA ethane, trimethylolpropane, other hexanetriols and pentaerythritol, under the conditions described.

Diisocyanates, in particular hexamethylene diisocyanate, isophorone diisocyanate, toluylene diisocyanate and diphenylmethane diisocyanate are preferably employed.

This method of covalent bonding of immunologically active substances (enzymes, antibodies) to the membrane surface is not only exceptionally simple but it provides a range of variation in respect of the chemical structure and the chain length of the linkers between the porous polymer membrane and the active substances which is unknown for the coupling reagents hitherto known. A plurality of methods is available for carrying out the binding of the active substances.

Thus, in a first method, the described amine-modified membrane can initially be impregnated with an approximately 0.1 to 1% strength aqueous solution of the isocyanate-bisulphite adduct. This impregnation takes place, for example, very simply by immersion of the membrane in a solution of this type. The membrane is then dried under suitable conditions, for example in an oven at 30 to 80° C. for a period of 5 to 120 minutes. The iramobilization of immunologically active substances can now take place simply by contacting a solution of these active substances with the membrane surface. The contacting takes place, for example, simply by impregnation or, when working with microtiler plates or bio dot apparatus, by sucking the active compound solution through.

In a second method, a common aqueous solution of the isocyanate-bisulphite adduct and of the biochemically active substance to be immobilized is prepared and contacted with the amine-modified membrane. In this case an excess of the bisulphite adduct over the required amount based on moles of active substance has proved advantageous.

The method according to the invention permits the entire range of immunochemical test methods, for example the immunological detection of pathogens for plants, humans and animals, the detection of active compounds in plants, humans and animals, the detection of impurities (for example plant protection agents) in soil and groundwater and other test methods.

The suitability of the methods according toi the invention for carrying out such immunochemical (immunodiagnostic) tests is explained in detail in the following examples.

The examples describe the following steps:

1. Preparation of amine-modified macroporous polymer membranes
2. Immunodiagnostic test methods using examples of mouse IgG
3. Comparison between adsorptive and covalent iramobilization.

Example 1

Preparation of an amine-modified polymer blend membrane

A high-speed stirrer (dissolver) was used to prepare a polymer casting solution from the following components:

| | |
|---|---|
| DRALON T ® (polyacrylonitrile) | 9.6 g |
| DESMODERM KBH ® (polyurethane, 20% in NMP) | 170.0 g |
| MOWILITH 50 ® (polyvinyl acetate, 25% in NMP) | 225.8 g |
| N-methylpyrrolidone (NMP) | 220.0 g |
| Silbond 600 AST (amine-modified silicate) | 293.4 g |
| Sodium dodecyl sulphate (SDS) | 3.9 g |
| 3,3',5,5'-Tetramethylbenzidine | 31.3 g |
| POLYMIN P ® (polyethyleneimine, 50% in water) | 2.1 g |

The chemical structures of the polymers used are described in German Offenlegungsschrift 3 809 523.

The casting solution was filtered (metal cloth, 25 μm mesh width) and degassed.

Membrane preparation

A supported membrane was prepared by the known method of precipitation coagulation in water. The following conditions were observed:

Support material: nonwoven polyester FO 2403 from Freudenberg
Wet application with knife: 300 μm
Coagulation bath: Water, 40° C.
Drying conditions: 60° C., 20 min This resulted in a macroporous polymer blend membrane which adhered to the nonwoven polyester, contained the indicator 3,3',5,5'-tetramethylbenzidine and was employed as carrier matrix for the following immunochemical detection reactions.

Example 2

Procedure for a sandwich ELISA for detecting mouse IgG

Commercially obtainable immunoglobulins were used to carry out an immunoassay on the sandwich ELISA principle with the polymer blend membrane as solid phase. The components used for the immunoassay, the prim. (capture) antibody, sec. (marker) antibody, antigen (Mouse IgG) were obtained from SIGMA Chemie GmbH, Deisenhofen.

The following specific antibodies were used:

1. As prim. antibody (capture antibody):

| Sigma No. | Type | Origin |
|---|---|---|
| M 3014 | a-mouse IgG whole molecule | Goat |
| M 9637 | a-mouse IgG whole molecule | Rabbit |

2. As sec. antibody (marker antibody):

| Sigma No. | Type | Origin | Marker |
|---|---|---|---|
| A 2028 | a-mouse IgG whole molecule | Rabbit | Peroxidase |
| A 4416 | a-mouse IgG whole molecule | Goat | Peroxidase |

3. As antigen (mouse IgG)

| Sigma No. | Type |
|---|---|
| I 5381 | Mouse IgG |

A plurality of combinations of prim. and sec. antibodies was used for applications.

| Prim. antibody | Antigen | Sec. antibody |
|---|---|---|
| M 3014 | I 5381 | A 2028 |
| M 3014 | I 5381 | A 4416 |
| M 9637 | I 5381 | A 4416 |

Procedure for the immunoassay methods:

The frame used for the assay membrane was a dot-blot apparatus from BioRad. A mild waterpump vacuum was applied for the filtration steps.

The polymer blend membrane was hydrated with 100 μm of H₂O per dot. Then the prim. antibody at a concentration of 1 mg/ml of water in a volume of 400 μm was filtered through the membrane. Subsequently serial dilutions of the antigen (mouse IgG) were sucked in a volume of 200 μl per dilution and different concentration through the membrane. After a washing step, the sec. antibody (POD marker) was filtered through the membrane. Finally, washing was carried out once with 500 μl of PBS/Tween and once with 500 μl of water, and the membrane was immersed in the substrate solution for the marker enzyme to develop the colour.

The results of the binding assay were determined in a pocket reflectometer.

Figure 2:
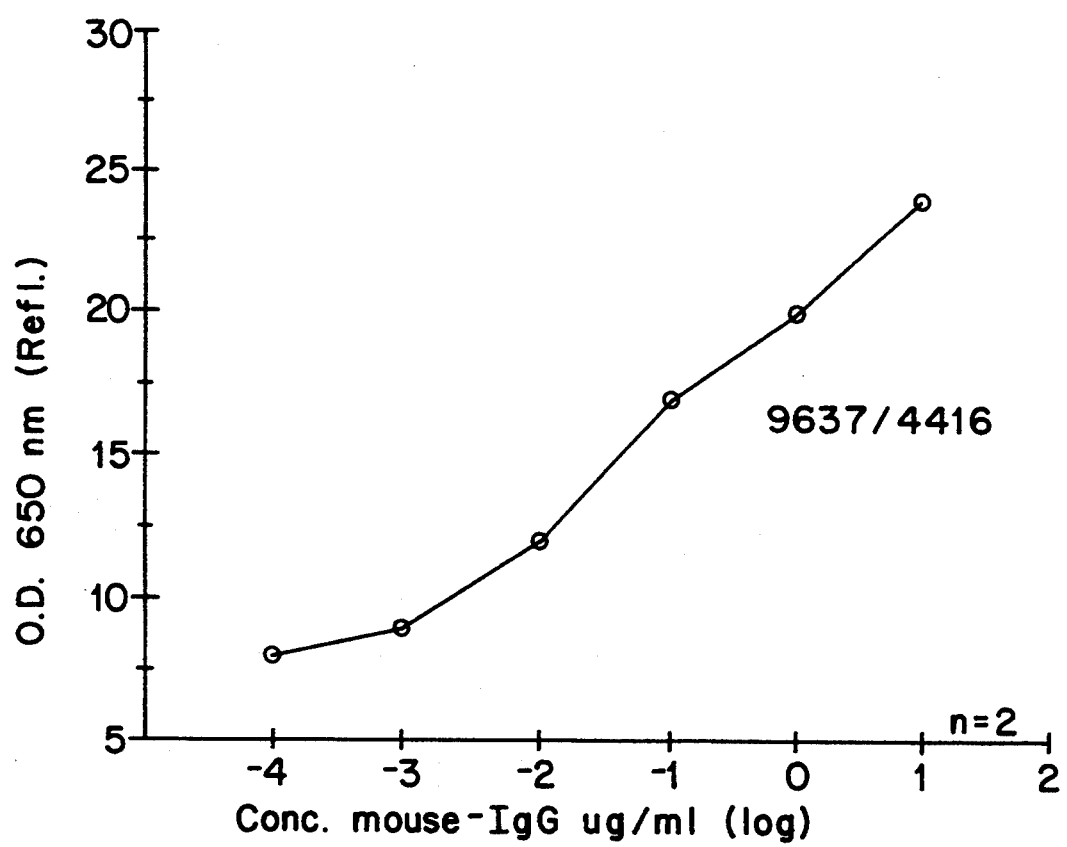
Figure 3:
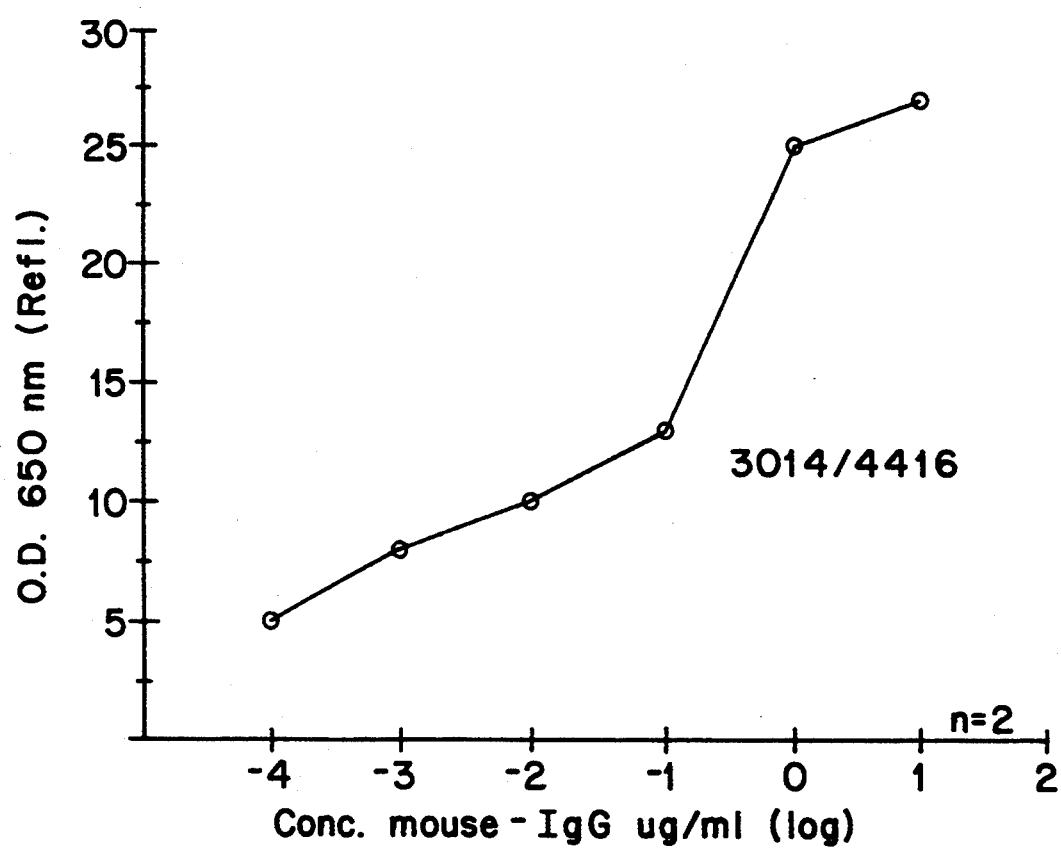

The results of the binding experiments are presented as follows (appended FIG. 1-3; conc. mouse IgG μg/ml (log)):
 FIG. 1: System M 3014/I 5381/A 2028
 FIG. 2: System M 3014/I 5381/A 4416
 FIG. 3: System M 9637/I 5381/A 4416

The example shows the excellent suitability of the membrane matrices according to the invention for immunoassays. The mouse IgG analyte can be detected reliably down to the nanogram range.

Besides water, the following buffer systems were used in Example 2:

PBS (phosphate-buffered physiological saline) 0.01 M phosphate (=0.008 M $K_2HPO_4$ and 0.002 M $NaH2PO4$) with 0.15 M NaCl at pH 7.4.

Acetate buffer substrate mixture (for POD reaction) 0.1 M Na acetate in $H_2O$, pH 6.0 (adjusted with 1 M citric acid); $H_2O_2$ (3.0%) was added at 1 ml per 1 as redox partner.

Tween 20 (polyoxyethylene sorbitan monolaurate, Sigma No.: P 1379) 0.01% in distilled $H_2O$.

Example 3 (for comparison)

Procedure for a sandwich ELISA to detect mouse IgG Example 2 was repeated but with the alteration that a polyvinylidene difluoride membrane from Millipore (Immobilon P) was used, not a polymer blend membrane according to the invention, as solid phase.

Before the assay procedure described in Example 1, the membrane was rendered lyophilic by sucking through 100 μl of ethanol. Since, in contrast to the polymer blend membranes according to the invention, the membrane contains no chromogen, it was immersed after the immunological reaction in a substrate solution which was prepared as follows:

Tetramethylbenzidine was dissolved in a concentration of 2 mg/ml in methanol (stock solution). The substrate solution was freshly prepared from 5 pans of stock solution, 3.75 parts of 0.4 M citrate buffer (pH 5.5), 11.3 parts of $H_2O$ and 0.025 part of 30% $H_2O_2$.

The blue coloured spots when each rapidly appeared became ever larger, less differentiated and, in some cases, merged with one another. Leaching out of the dye into the substrate solution led to the latter becoming deep blue, and thus the entire membrane in turn was coloured blue.

Moreover, after the membrane was dried, the colour was stable for only a few minutes so that no reflectometric evaluation was possible. In contrast thereto, coloured spots remain stable and can be evaluated on the polymer blend membranes according to the invention for several days, often for up to some weeks.

Example 4

Immunologically active substances are sufficiently firmly immobilized on the surface of the polymer blend membranes according to the invention. The iramobilization can be further improved by pretreatment with isocyanate-bisulphite adducts.

This effect is demonstrated by Example 4. A marker antibody (Sigma A 9169, type: a-rabbit IgG, origin: goat, marker: peroxidase) was immobilized as described in Example 2 on the surface of a polymer blend membrane according to Example 1. In one case the membrane was untreated and in the other it was pretreated with a 0.2% strength aqueous solution of the bisulphite adduct of hexamethylene diisocyanate. The pretreatment was carried out in such a way that the membrane was impregnated with the bisulphite adduct solution by immersion, and the membrane was subsequently dried in a circulating air oven at 60° C. for 1 h.

After adsorption on the membrane surface, the durability of the iramobilization was checked by washing up to eight times with various buffers and reagents and, after each of the washing steps, detection by means of an enzyme reaction of the peroxidase (POD) used and $TMB/H_2O_2$ as redox partner. The following table indicates the number of washing steps after which a distinct attenuation of the blue coloration is evident.

| Medium | 1 | 2 | 3 | 4 | 5 | 6 |
| --- | --- | --- | --- | --- | --- | --- |
| Membrane untreated | 4 | 6 | n.w. | n.w. | 4 | 3 |
| Membrane pretreated | n.w. | n.w. | n.w. | n.w. | 6 | 4 | n.w. = not washed out

Buffers and reagents used as washing media:
1=$H_2O$
2=$H_2O$ with 0.1% Tween 20
3=PBS
4=PBS with 0.1% Tween 20
5=acetate buffer
6=carbonate buffer (0.1 M $NaHCO_3$ in $H_2O$, pH 9.6, adjusted with sodium hydroxide solution)

Appendix:

Chemical structures of the polymers which are preferably employed

Polyurethane (DESMODERM KBH®, Bayer AG)

Thermoplastic polyaddact which was obtained by reaction of 75 parts of a polyester of adipic acid, 70 mol% of ethylene glycol and 30 mol% of 1,4-butanediol (MW =2000), 25 parts of a polyester of adipic acid and 1,4-butanediol (MW=2250), 25 parts of 1,4-butanediol and 85 parts of diphenylmethane diisocyanate.

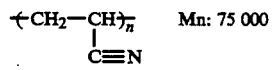

DRALON U ® (Bayer AG)

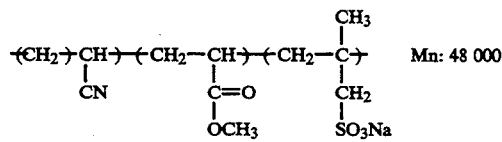

91.5% by weight   5.0% by weight   3.5% by weight

DRALON A ® (Bayer AG)

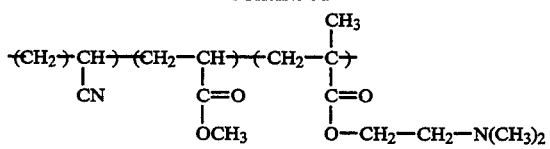

91.4% by weight  4.9% by weight  3.7% by weight

MOWILITH 50 ® (polyvinyl acetate Hoechst AG)

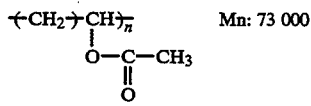  Mn: 73 000

What is claimed is:

1. In an immunoassay comprising contacting a macroporous membrane to which an enzyme or antibody is absorbed with a liquid putatively containing an antigen and detecting the presence of the antigen, the improvement comprising utilizing as the macroporous membrane a macroporous filler-containing membrane where the membrane is prepared by (1) forming an unstable mixture of at least two polymers which are immisible in solution, (2) dispersing insoluble fillers into the unstable mixture of such immisible polymers thereby converting the mixture into a stable homogeneous mixture, and (3) applying such stable mixture to a substrate as a casting solution by precipitation coagulation.

2. The method of claim 10, wherein the insoluble fillers comprise from 5 to 500% by weight based on the total weight of the polymers in the membrane.

3. The method of claim 1, wherein the fillers are highly dispersed fillers and are employed in amounts of 5 to 50% by weight.

4. The method of claim 1, wherein the fillers have lower specific surface areas and are employed in amounts of 35 to 500% by weight.

5. The method of claim 1, wherein the polymers are selected from the group consisting of combinations of
   a) cellulose esters/polyvinyl esters,
   b) polyurethane/polyacrylates or acrylic copolymers,
   c) polycarbonate copolymers/polyurethane,
   d) polyvinyl derivatives/polysulphones,
   e) polyamides or polyimides/polystyrene or styrene copolymers,
   f) poly-para-dimethylphenylene oxide/polyvinylidene fluoride,
   g) polysulphone/polyacrylonitrile, and
   h) poly(ethersulphone)/anionically modified polyacrylonitrile.

6. The method of claim 1 wherein the macroporous polymer membrane contains an integrated chromogen.

7. The method of claim 1, wherein the macroporous membrane has a surface modified by free amino groups.

8. The method of claim 8, wherein bisulphite adducts of isocyanates are employed for the covalent binding of the enzymes or antibodies to the free amino groups on the surface of said macroporous membrane.

9. The method of claim 1, wherein the insoluble fillers are selected from the group consisting of talc, titanium dioxide, barium sulphate, silicon dioxide, microcrystalline cellulose, zeolite, bentonite, highly dispersed silica and quartz.

10. The immunoassay of claim 1 wherein the macroporous filler-containing membrane contains free amino groups.

11. The immunoassay of claim 1 wherein the filler in the macroporous filler-containing membrane is an amino-modified filler.

12. The immunoassay of claim 1 wherein the enzyme or antibody is attached to the membrane through a covalent linkage.

13. The method of claim 1, wherein the forming step comprises forming an unstable mixture of three immiscible polymers.

* * * * *

UNITED STATES PATENT AND TRADEMARK OFFICE
CERTIFICATE OF CORRECTION

PATENT NO. : 5,420,047
DATED : May 30, 1995
INVENTOR(S) : Brandt, et al.

It is certified that error appears in the above-indentified patent and that said Letters Patent is hereby corrected as shown below:

Item [56],
Title Page  U.S. PATENT DOCUMENTS: After " 5,122,452 " delete " 1/1992 " and substitute -- 6/1992 --

Col. 11, claim 2 line 1  Delete claim " 10 " and substitute claim -- 1 --

Col. 12, line 19  Delete " polymer "

Col. 12, line 22  Delete claim " 8 " and substitute claim -- 7 --

Signed and Sealed this

Twelfth Day of September, 1995

Attest:

BRUCE LEHMAN

Attesting Officer  Commissioner of Patents and Trademarks